(12) United States Patent
Jafarzadeh

(10) Patent No.: US 10,835,410 B2
(45) Date of Patent: Nov. 17, 2020

(54) PHOTOTHERAPY SYSTEM FOR TREATING NASAL DISORDERS

(71) Applicant: Cosmetic Edge Pty Ltd, Kew (AU)

(72) Inventor: Mathew Jafarzadeh, Kew (AU)

(73) Assignee: Cosmetic Edge Pty Ltd, Victoria (AU)

( * ) Notice: Subject to any disclaimer, the term of this patent is extended or adjusted under 35 U.S.C. 154(b) by 125 days.

(21) Appl. No.: 16/068,354

(22) PCT Filed: Jan. 6, 2017

(86) PCT No.: PCT/AU2017/050013
§ 371 (c)(1),
(2) Date: Jul. 5, 2018

(87) PCT Pub. No.: WO2017/117634
PCT Pub. Date: Jul. 13, 2017

(65) Prior Publication Data
US 2018/0303654 A1    Oct. 25, 2018

(30) Foreign Application Priority Data

Jan. 6, 2016 (AU) .................................. 2016900030

(51) Int. Cl.
| | | |
|---|---|---|
| A61F 5/08 | (2006.01) |
| A61N 5/06 | (2006.01) |
| A61F 9/02 | (2006.01) |
| A61F 9/04 | (2006.01) |
| A61N 5/067 | (2006.01) |

(52) U.S. Cl.
CPC ................ *A61F 5/08* (2013.01); *A61F 9/029* (2013.01); *A61F 9/04* (2013.01); *A61N 5/0625* (2013.01); *A61N 2005/067* (2013.01); *A61N 2005/0647* (2013.01); *A61N 2005/0652* (2013.01)

(58) Field of Classification Search
CPC ... A61F 5/08; A61F 9/029; A61F 9/04; A61N 2005/0647; A61N 2005/0652; A61N 2005/067; A61N 5/0625; A61N 5/06–2005/073; A61B 18/20–28
See application file for complete search history.

(56) References Cited

U.S. PATENT DOCUMENTS

| | | | |
|---|---|---|---|
| 5,558,090 A | * | 9/1996 | James ............... A61M 16/0497 128/207.17 |
| 5,683,436 A | | 11/1997 | Mendes et al. |
| 6,684,883 B1 | | 2/2004 | Burns |

(Continued)

FOREIGN PATENT DOCUMENTS

| | | |
|---|---|---|
| KR | 20040023463 | 3/2004 |
| KR | 20110100122 A | 9/2011 |

(Continued)

OTHER PUBLICATIONS

The Glow Company, Light Up Faces, Mar. 25, 2015, https://web.archive.org/web/20150324121748/https://www.glow.co.uk/light-up-faces.html (Year: 2015).*

(Continued)

*Primary Examiner* — Jonathan T Kuo
(74) *Attorney, Agent, or Firm* — K&L Gates LLP

(57) ABSTRACT

A system, comprising a support adapted to be worn on a head and support a light source to administer an effective amount of light to a nose of the head sufficient to treat a nasal disorder.

21 Claims, 8 Drawing Sheets

(56) References Cited

U.S. PATENT DOCUMENTS

| | | | |
|---|---|---|---|
| 9,227,082 B2* | 1/2016 | McDaniel | A61K 41/0057 |
| 10,478,636 B2* | 11/2019 | Choi | A61N 5/0603 |
| 2006/0206173 A1* | 9/2006 | Gertner | A61N 5/0616 |
| | | | 607/88 |
| 2010/0076529 A1* | 3/2010 | Tucker | A61N 5/0616 |
| | | | 607/90 |
| 2010/0174222 A1* | 7/2010 | McDaniel | A61B 18/203 |
| | | | 604/20 |
| 2012/0160240 A1 | 6/2012 | Spano | |
| 2015/0173933 A1 | 6/2015 | Castillo | |
| 2015/0216710 A1 | 8/2015 | Wanderer et al. | |
| 2015/0335910 A1* | 11/2015 | Tapper | A61N 5/0616 |
| | | | 607/90 |
| 2016/0166847 A1* | 6/2016 | Choi | A61N 5/0603 |
| | | | 607/92 |

FOREIGN PATENT DOCUMENTS

| | | |
|---|---|---|
| KR | 101558180 | 10/2015 |
| KR | 20160095574 | 8/2016 |
| WO | WO 2004/043543 A1 | 5/2004 |
| WO | WO 2015/178960 A2 | 11/2015 |
| WO | WO2015174556 | 11/2015 |

OTHER PUBLICATIONS

International Search Report for Application No. PCT/AU2017/050013, dated Mar. 28, 2017 (5 pages).
Written Opinion for Application No. PCT/AU2017/050013, dated Mar. 28, 2017 (13 pages).
International Preliminary Report on Patentability for Application No. PCT/AU2017/050013, dated Jan. 8, 2018 (6 pages).

* cited by examiner

PHOTOTHERAPY SYSTEM FOR TREATING NASAL DISORDERS

FIELD

The present invention relates to a phototherapy system for treating nasal disorders.

BACKGROUND

Nasal disorders may be categorised as "cosmetic" or "functional." Cosmetic disorders of the nose include age-related increases in nasal size and changes in nasal shape, as well as cancerous or noncancerous nasal masses, such as nasal lipoma. Functional disorders of the nose include nasal obstruction, nasal congestion, and nasal swelling or inflammation.

Conventional treatments for cosmetic and functional nasal disorders include rhinoplasty. Rhinoplasty is invasive plastic surgery performed to make changes to the internal or external structures of the nose to improve the cosmetic appearance of the nose, or to assist the functioning of the nose. Rhinoplasty has various drawbacks including post-operative nasal swelling that obstructs nasal breathing, and which is unsightly, painful and uncomfortable.

In this context, there is a need for improved treatments and therapies for cosmetic and functional nasal disorders.

SUMMARY

According to the present invention, there is provided a system, comprising a support adapted to be worn on a head and support a light source to administer an effective amount of light to a nose of the head sufficient to treat a nasal disorder.

The support may be further adapted to adjustably or conformably support the light source in contacting or non-contacting relationship with one or more internal nasal surfaces, external nasal surfaces, or combinations thereof.

The support may comprise a headband, a headset, an eyeglass frame, a goggle frame, a face mask, a hat, or combinations thereof.

The support may further comprise a nosepiece adapted to support the light source.

The support may further comprise one or more eye shields.

The light source may comprise one or more light emitting diodes (LEDs), laser diodes, or combinations thereof.

The light source may comprise multiple LEDs that are collectively or individually controllable.

The light may have a wavelength between 300 nm and 1000 nm, for example, between 600 nm and 860 nm. The light may have peak intensity at a wavelength around 635 nm.

The nasal disorder may comprise a cosmetic or functional nasal disorder selected from nasal deformity, nasal mass, nasal lipoma, nasal swelling, nasal inflammation, nasal obstruction, nasal congestion, nasal trauma, nasal pain, and combinations thereof.

The system may further comprise a controller adapted to control the light source.

The controller may be adapted to control one or more parameters of the light source selected from wavelength (nm), light output frequency (continuous versus pulsed), power output (mW), power density (W/cm$^2$), energy density (J/cm$^2$), treatment time, total energy delivered (J), and combinations thereof.

The system may further comprise a user interface connected to the controller.

The present invention also provides a method of treating a nasal disorder using the system described above.

The present invention further provides a system, comprising:
- a headband to fit around a forehead of a head;
- an adjustable nosepiece extending downwardly from the headband to support LEDs closely adjacent a nose of the head; and
- a controller to control the LEDs to administer an effective amount of light to treat a disorder of the nose.

The adjustable nosepiece may have an inverted T-shape, and may comprise a stem extending vertically downwards from the forehead over a tip of the nose, and a pair of wings extending horizontally from a lower end of the stem over a pair of nostrils of the nose.

The stem may be vertically adjustable over the tip of the nose, and the pair of wings may be horizontally adjustable over the pair of nostrils.

The nosepiece may be removably connectable to the headband.

The controller may comprise a remote Bluetooth controller to wirelessly control the LEDs.

The present invention also provides a system, comprising:
- eyeglasses wearable by a user;
- a nosepiece adjustably attachable to the eyeglasses to cover a nose of the user;
- LEDs in the nosepiece to direct light over the user's nose;
- a controller in the nosepiece to control the LEDs to administer an effective amount of light to treat a disorder of the user's nose.

The system may further comprise a liner adjustably attachable to one or both of the nosepiece and the eyeglasses between the LEDs and the user's nose.

One or both of the nosepiece and the liner may be consumable or disposable.

One or both of the nosepiece and the liner may be deformable to adjustably conform to the user's nose.

One or both of the nosepiece and the liner may comprise a flexible material supported by a deformable frame.

One or both of the nosepiece and the liner may have an inverted T-shape, and may comprise a stem extending vertically downwards from the forehead over a tip of the user's nose, and a pair of wings extending horizontally from a lower end of the stem over a pair of nostrils of the user's nose.

The liner may have the inverted T-shape and the nosepiece may have a triangular curved shape.

The controller may comprise a printed circuit board (PCB) having a Bluetooth interface.

BRIEF DESCRIPTION OF DRAWINGS

Embodiments of the invention will now be described by way of example only with reference to the accompanying drawings, in which.

DESCRIPTION OF EMBODIMENTS

Figure 1:
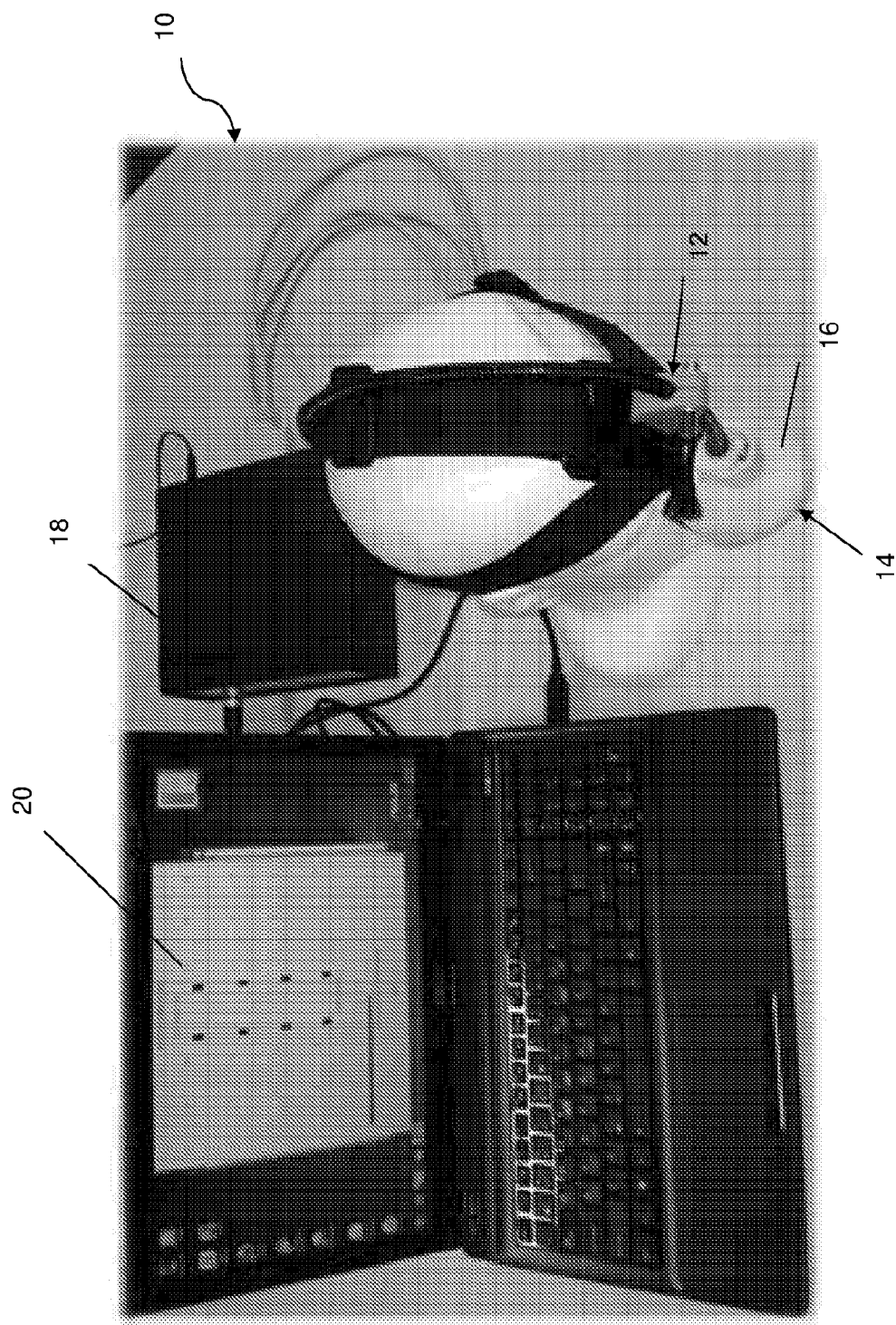
FIG. 1 is a photograph of a phototherapy system for treating nasal disorders according to an embodiment of the present invention.

Referring to the drawings, a phototherapy system 10 according to an embodiment of the present invention generally comprises a support 12 adapted to be worn on a human head and support a light source 14 to administer an effective amount of light to a nose of the head sufficient to treat a nasal disorder or condition. The nasal disorder may comprise a cosmetic or functional nasal disorder selected from nasal deformity, nasal mass, nasal lipoma, nasal swelling, nasal inflammation, nasal obstruction, nasal congestion, nasal trauma, nasal pain, and combinations thereof. Other equivalent or alternative nasal disorders, deformities, diseases, and conditions may also be treated using the system 10.

In the context of this specification, the term "effective amount" includes a non-damaging but sufficient dose of light to provide the desired therapeutic effect to treat the nasal disorder. Those skilled in the art will appreciate that the exact dosage amount of light required will vary based on a number of factors (including, but limited to, type of nasal disorder, individual patient characteristics, wavelength (nm), light output frequency (continuous versus pulsed), power output (mW), skin penetration (mm), spot diameter (cm), spot size ($cm^2$), power density ($W/cm^2$), energy per point (J), energy density ($J/cm^2$), treatment time per point (s), number of points, total energy delivered (J), application mode (skin contact versus non-contact), etc), and thus it is not possible to specify an exact "effective amount". However, for any given nasal disorder, deformity or condition, an appropriate "effective amount" may be determined by one of ordinary skill in the art using only routine trial and experimentation.

The support 12 may be further adapted to adjustably or conformably support the light source 14 in contacting or non-contacting relationship with one or more internal nasal surfaces, external nasal surfaces, or combinations thereof. The support 12 may comprise a headband, a headset, an eyeglass frame, a goggle frame, a face mask, a hat, or combinations thereof. For example, as illustrated in FIG. 1, the support 12 may comprise a headset. Other equivalent or alternative supports for the light source 14 may also be used.

Figure 2:
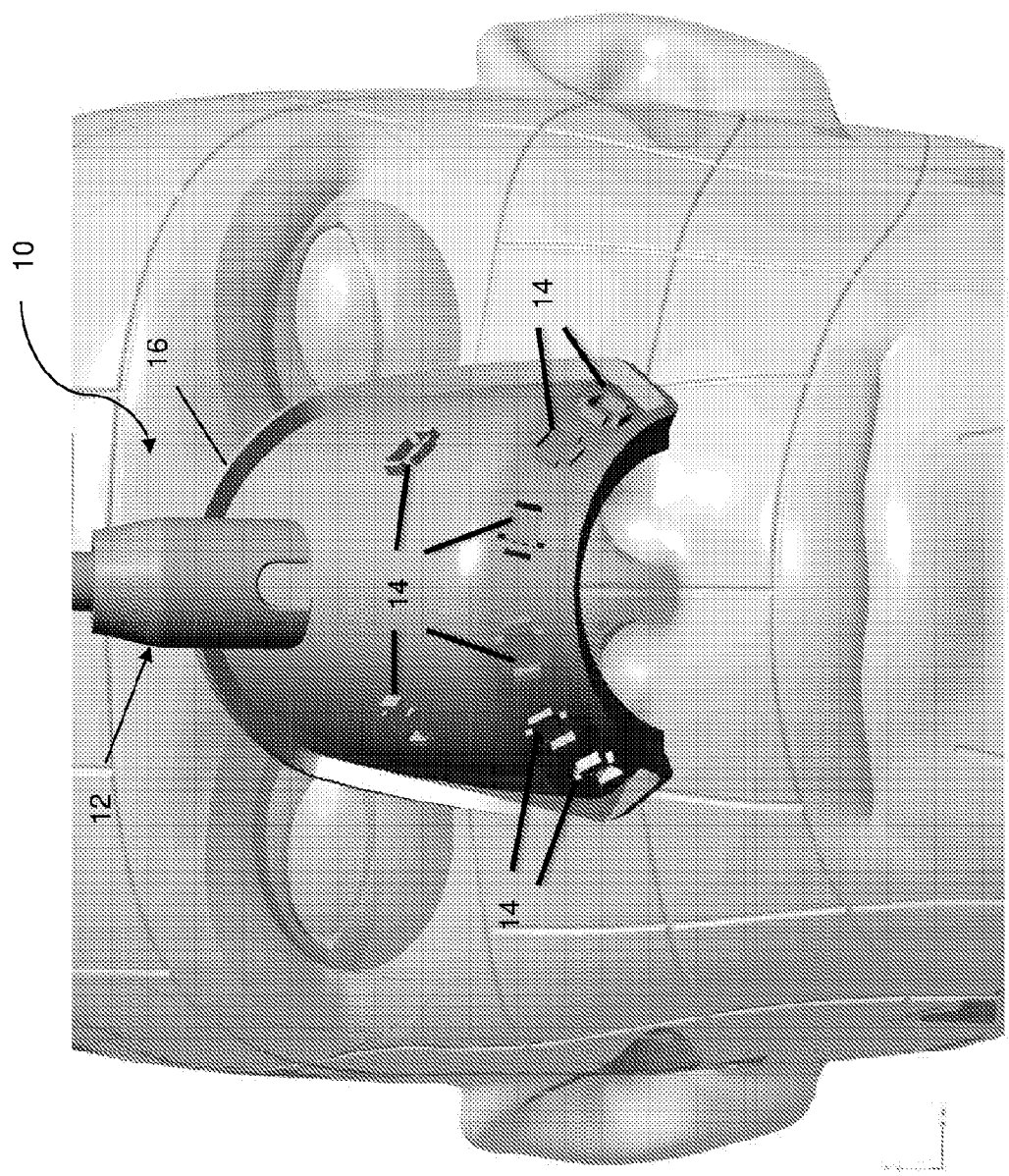
FIG. 2 is a front view of a nosepiece supporting LEDs of the system.

As best seen in FIG. 2, the support 12 may further comprise a nosepiece 16 adapted to support the light source 14. The support 12 may further comprise one or more eye shields (not shown). The light source 14 may comprise one or more light emitting diodes (LEDs), laser diodes, or combinations thereof. For example, as illustrated in FIG. 1, the light source 14 may comprise multiple LEDs 14 that are collectively or individually controllable. Other equivalent or alternative light sources may also be used. Optionally, the system 10 further comprises optics, such as lenses, filters, etc (not shown) adapted to modify or control optical characteristics or parameters of the light produced by the light source 14.

The light source 14 may be adapted to produce light in a broad therapeutic window comprising a wavelength between 300 nm and 1000 nm, for example, between 600 nm and 860 nm. The light may have peak intensity at a wavelength around 635 nm. Other equivalent or alternative wavelength ranges or peak intensities may also be used.

The phototherapy system 10 may further comprise a controller 18 adapted to control the light source 14. For example, when the light source 14 comprises multiple LEDs 14, the controller 18 may comprise a LED driver circuit controlled by a microcontroller that is adapted to control the LEDs 14 individually. Other equivalent or alternative controllers may also be used. The controller 18 may be adapted to control one or more dosage parameters of the light source 14 selected from wavelength (nm), light output frequency (continuous versus pulsed), power output (mW), power density ($W/cm^2$), energy density ($J/cm^2$), treatment time, total energy delivered (J), and combinations thereof. Other equivalent or alternative dosage parameters may also be used.

Figure 3:
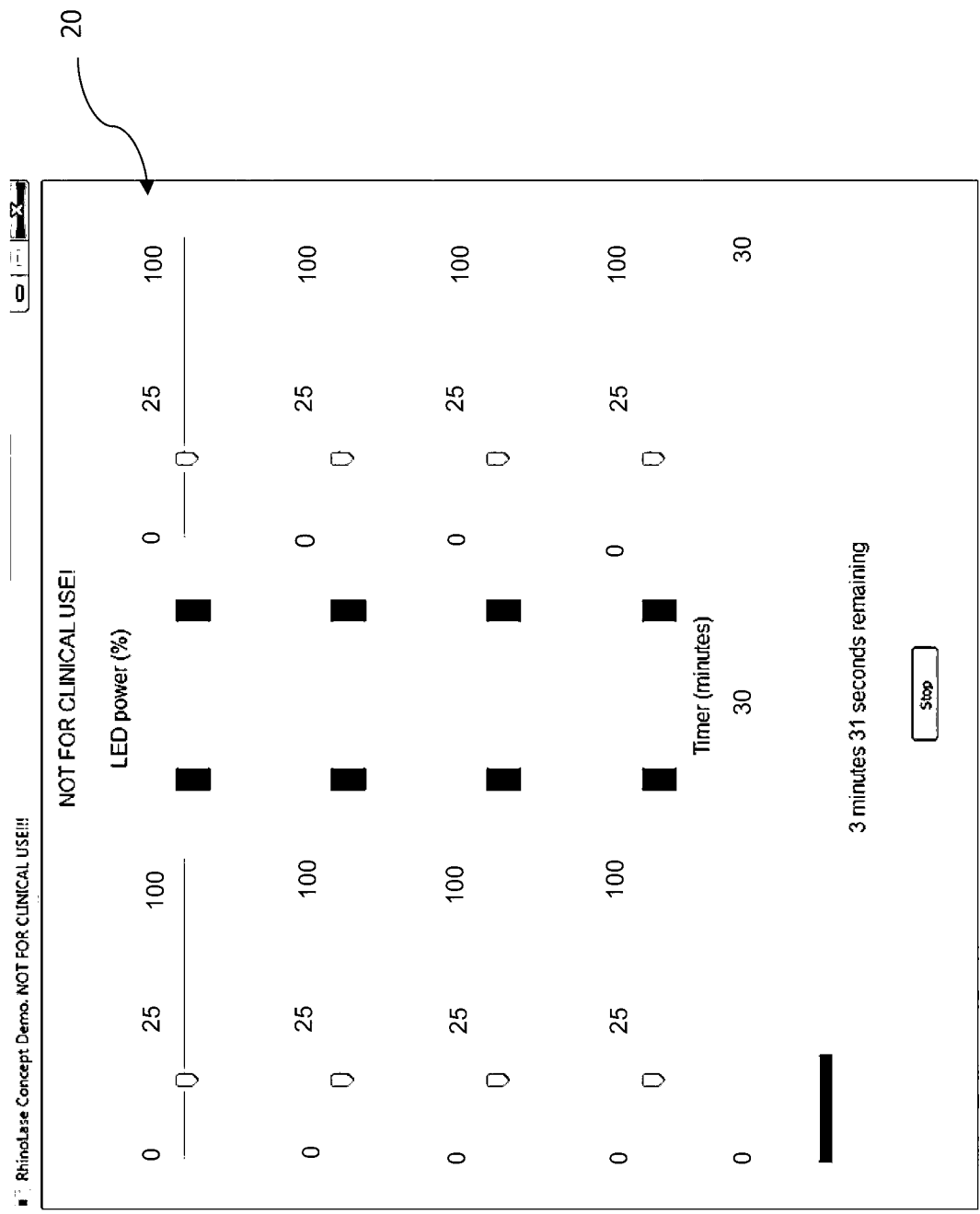
FIG. 3 is a user interface for controlling the LEDs of the nosepiece.

The system 10 may further comprise a user interface 20 connected to the controller 18. FIG. 3 illustrates an example user interface 20 that may be adapted to control power output (%) of individual LEDs 14 supported in the nosepiece 16. The user interface 20 may further be adapted to control the treatment time. Other equivalent or alternative control user interfaces may also be used.

The present invention also provides a method of treating a nasal disorder using the system 10 described above. The treatment protocol may be determined by routine trial and experimentation based on the factors described above for determining the effective amount of light to be administered by the system 10. The controller 18 may be programmed to control the light source 14 automatically based on a predetermined treatment protocol.

Figure 4:
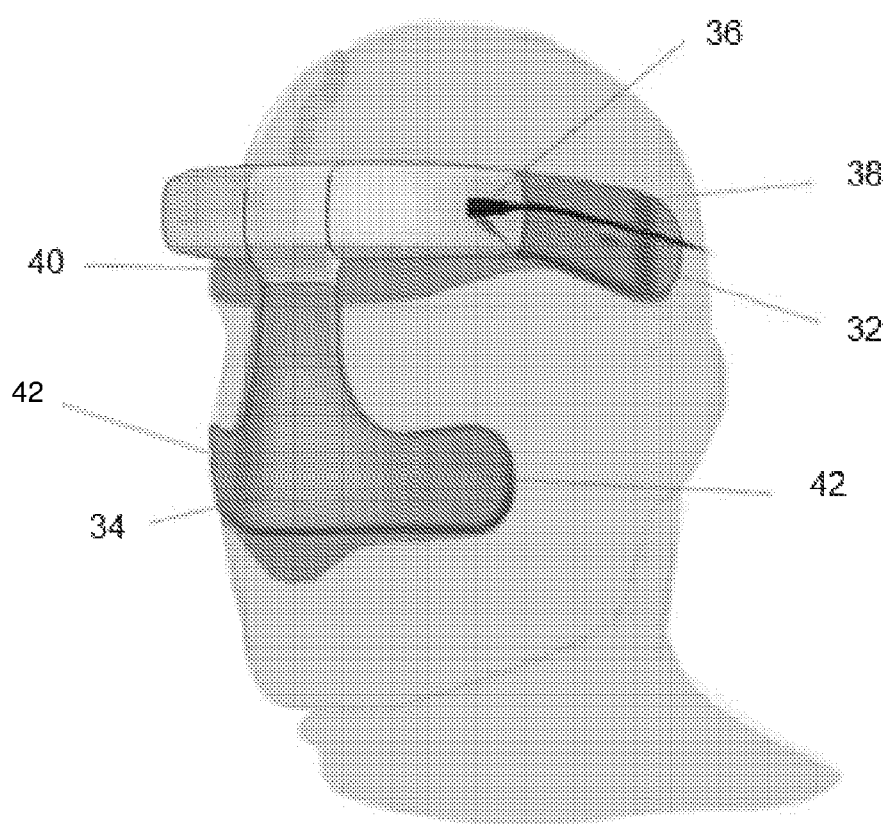
FIG. 4 is a schematic diagram of another embodiment of the phototherapy system.

FIG. 4 illustrates another embodiment of a phototherapy system 30 that may comprise a headband 32 to fit around a forehead of a head of a wearer, and an adjustable nosepiece 34 extending downwardly from the headband 32 to support LEDs (not shown) closely adjacent a nose of the head when the wearer is in a reclined position. The system 30 may further comprise a controller (not shown) to selectively and individually control the LEDs to administer an effective amount of light to treat a disorder of the nose. A power source for the LEDs, for example one or more batteries, may be provided in the headband 32 and/or adjustable nosepiece 34. Alternatively, the LEDs may be powered by a remote DC power supply connected to the headband 32 by a cable 36. A pair of cable-routing guides 38 may be provided on the headband 32. To ensure suitable light quality is provided to treat the nasal disorder or condition, the LEDs may have a predetermined service life, for example around 50 hours, after which time the adjustable nosepiece 34 may be replaceable. The controller may comprise a timer and may be configured to automatically stop operation of the LEDs after the predetermined service life, or a predetermined number of treatments.

Figures 8A, 8B, 8C:
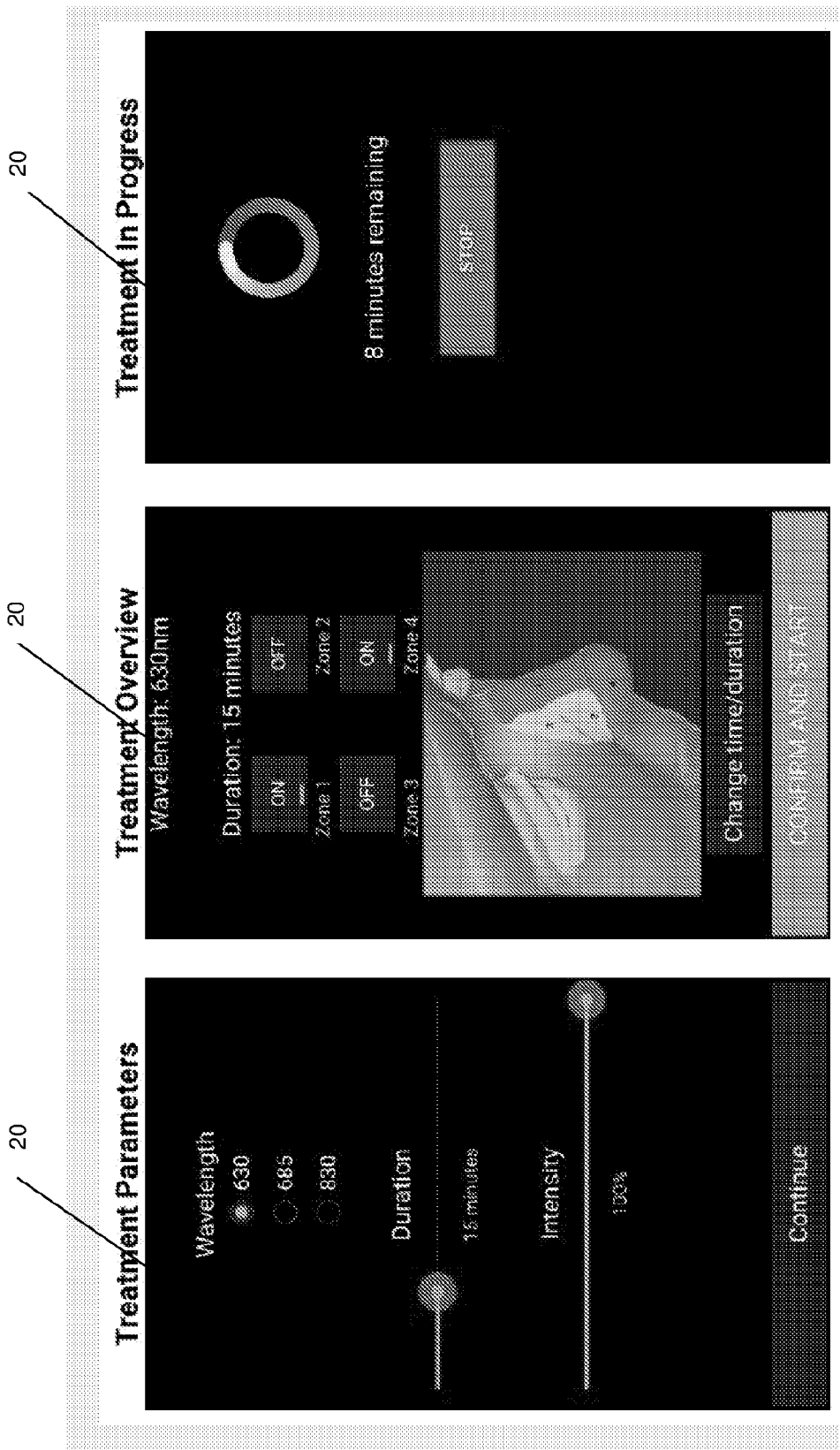
FIGS. 8*a* to 8*c* are example interactive user interfaces for controlling the phototherapy systems.

The adjustable nosepiece 34 may have an inverted T-shape, and may comprise a stem 40 extending vertically downwards from the forehead over a tip of the nose, and a pair of wings 42 extending horizontally from a lower end of the stem over a pair of nostrils of the nose. The stem 40 may be vertically adjustable, for example vertically slidable, over the tip of the nose, and the pair of wings 42 may be horizontally adjustable and three-dimensionally conformable or deformable over the pair of nostrils. Alternatively, the stem 40 may have a fixed length, and a plurality of different adjustable nosepieces 34 having different lengths may be provided to accommodate different nose lengths. The adjustable nosepiece 34 may be removably connectable to the headband 32. The controller may comprise a remote wireless, for example Bluetooth, controller to wirelessly control the LEDs. A PCB (not shown) comprising a Bluetooth interface may be provided in the headband 32 or adjustable nosepiece 34. The remote Bluetooth controller may have a display screen to display an interactive user interface to enable a professional practitioner, for example a plastic surgical skincare specialist or aesthetician, to select a suitable phototherapy dosage for individual subjects. The remote Bluetooth controller may comprise a computer device, for example, a desktop computer, a laptop computer, a tablet computer, a smartphone, and combinations thereof. Example user interfaces 20 displayed by the remote Bluetooth controller are illustrated at FIGS. 8a to 8c. The LEDs may be selectively controllable individually or in predetermined groups to provide to selected or predetermined nasal treatment areas, for example the nose tip, the nose bridge, one or both nostrils, and combinations thereof. The headband 32 may be formed as a moulding of semi-rigid, resilient plastics material. The adjustable nosepiece 34 may be formed as a moulding of a flexible plastics material or rubber, and a deformable metal skeleton may be provided in or on the flexible material to adjustably conform the adjustable nosepiece 34 to different three-dimensional nose shapes.

The adjustable nosepiece 34 may be flushed mounted in a recess or joggle in the headband 32 to ensure a close fit to the nose. A finger groove may be provided in the headband 32 behind the recess for easy removal and attachment of the adjustable nosepiece 34. The adjustable nosepiece 34 may be formed of an opaque material to hide the LEDs and other internal components.

The headband 32 may comprise a semicircular arc with widened end portions for firm retention of the headband 32 on the forehead. The pair of wings 42 of the adjustable nosepiece 34 may also comprise widened end portions to aid adjustment over the pair of nostrils and to accommodate different nose widths. The adjustable nosepiece 34 may further comprise a consumable or disposable thin liner (not shown) for hygiene, and to control spacing between the LEDs and the nose by providing a constant offset distance between the LEDs and external surfaces of the nose. The liner may comprise hygienic paper with deformable wire framing to three-dimensionally conform the liner to the nose of a wearer. Alternatively, the liner may comprise a preformed, flat-pack flexible material. A plurality of liners having different shapes and lengths may be provided to accommodate different nose shapes and sizes. The liner is transmissive to light, for example by comprising a transparent or translucent material, and/or cut-outs in the material. In use, the headband 32 and the adjustable nosepiece 34 may be worn over a pair of safety glasses to shield the eyes of the wearer. Alternatively, a pair of stick-on or adhesive laser eye shields (not shown) may be placed over the eyes of the wearer instead of the safety glasses to provide eye protection. A thermostat or heat sensor may be provided in or on the adjustable nosepiece 34 to provide thermal safety by preventing tissue of the nose overheating or exceeding a predetermined threshold temperature during use.

Figure 5:
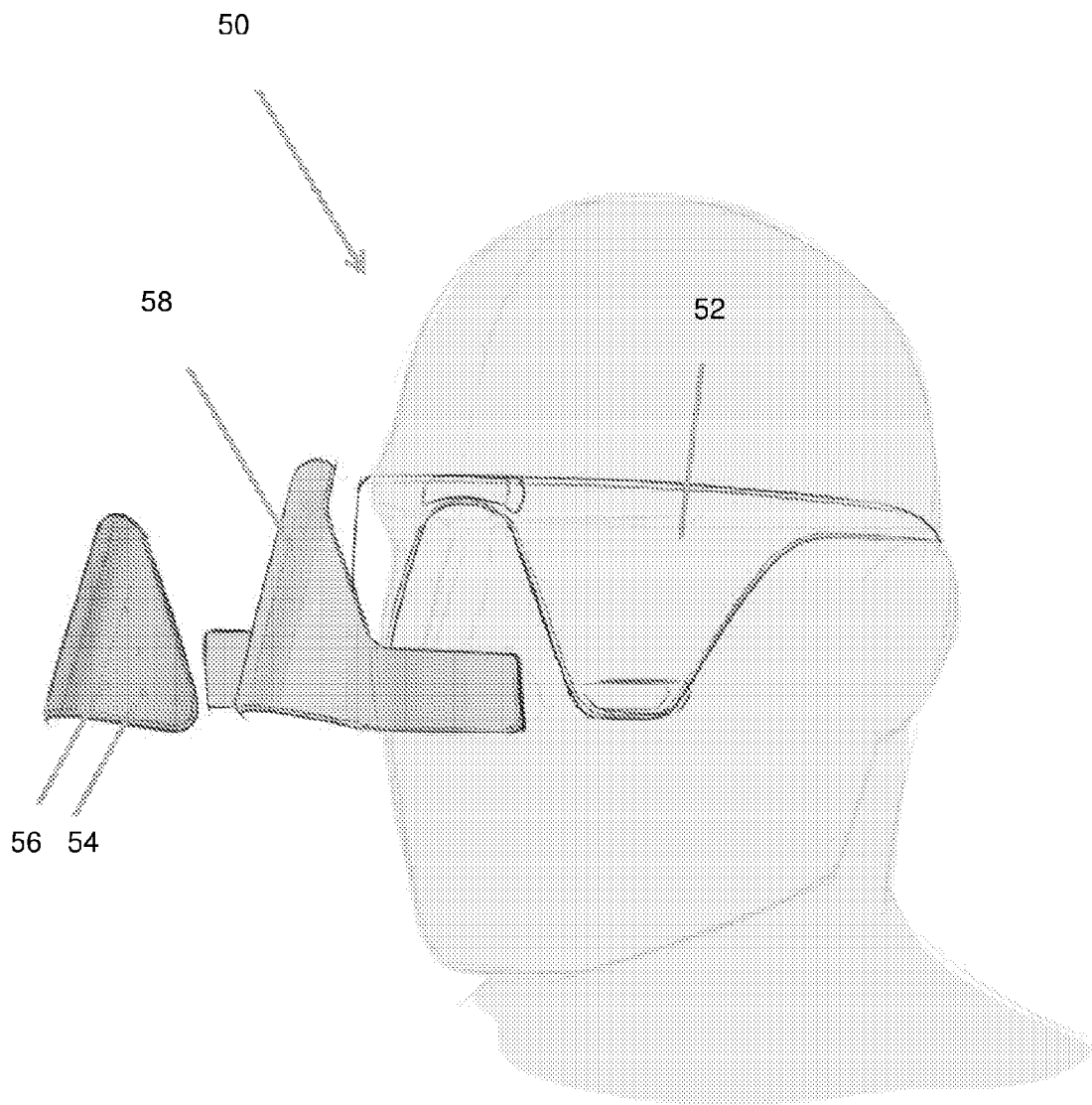
FIGS. 5 to 7 are front perspective views of further embodiments of the phototherapy system.
Figure 6:
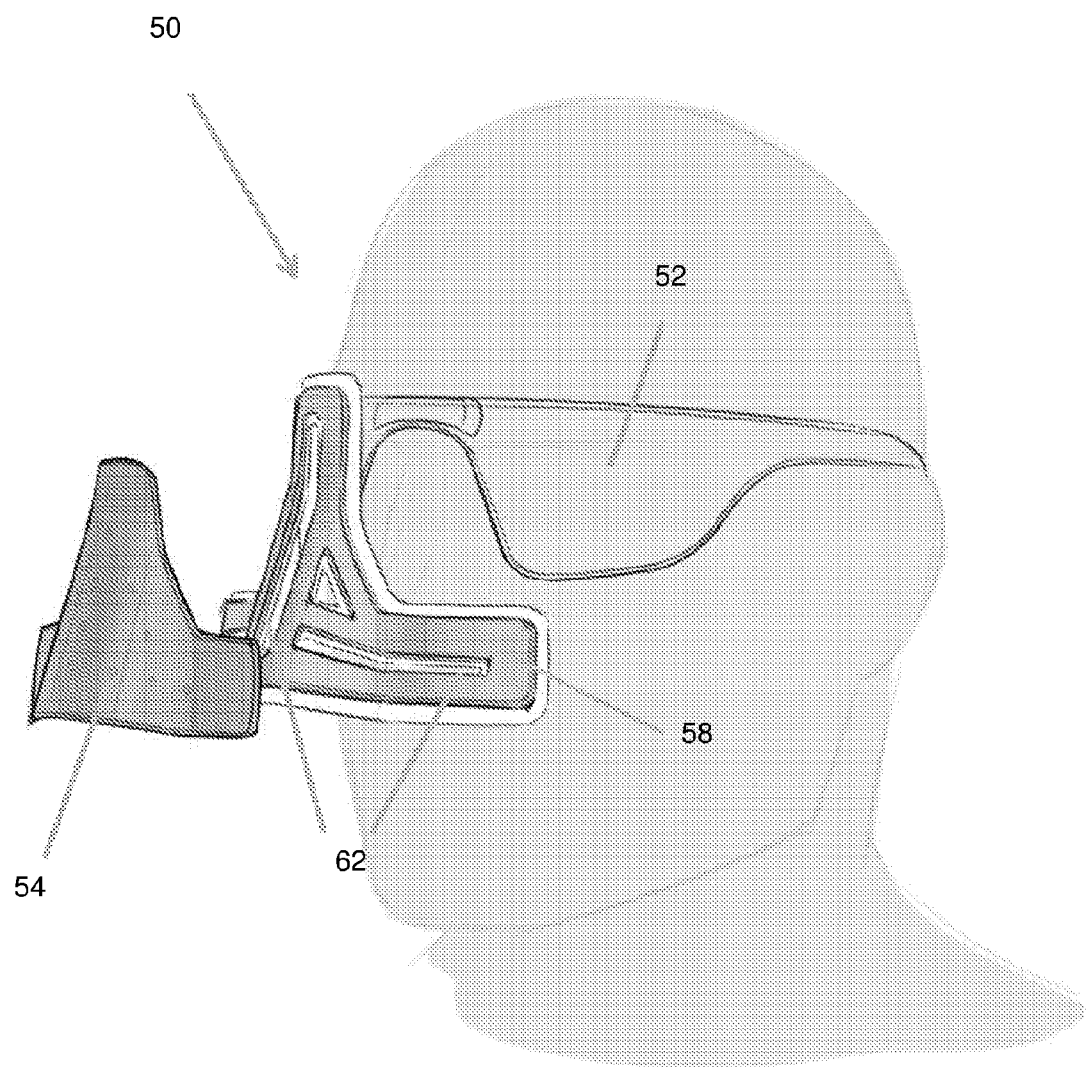
Figure 7:
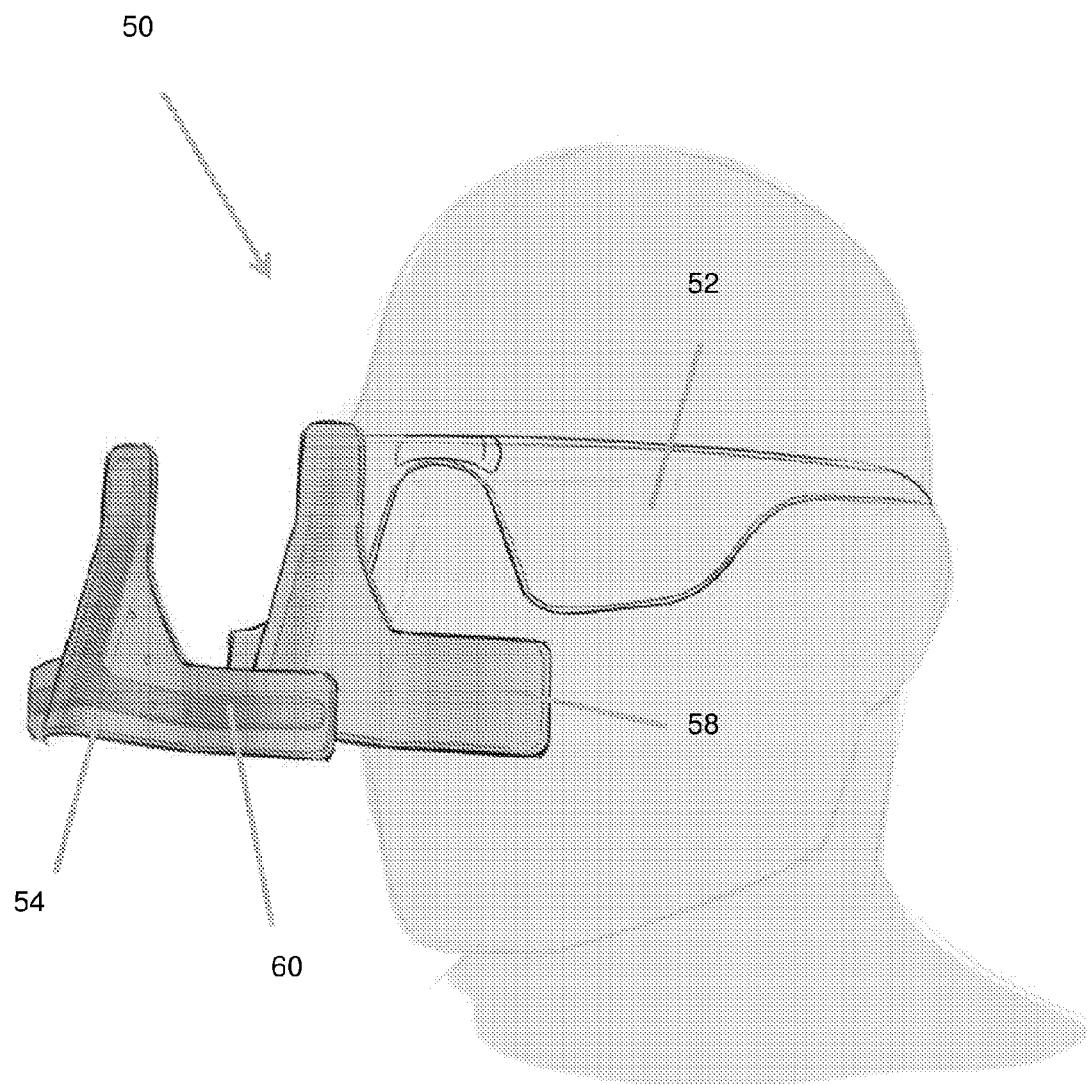

FIGS. 5 to 7 illustrate further embodiments of phototherapy systems 50. Each system 50 may generally comprise eyeglasses 52 wearable by a user, and a nosepiece 54 adjustably attachable to the eyeglasses 52 to cover a nose of the user. LEDs 56 may be provided in or on internal surfaces of the nosepiece 54 to direct light over and around the user's nose. A controller (not shown) may be in the nosepiece 54 to control the LEDs to administer an effective amount of light to treat a disorder of the user's nose. The controller may comprise a PCB having a Bluetooth interface to a remote controller. The remote controller may comprise a computer device having a display screen, for example a touchscreen, for displaying the user interfaces 20 illustrated in FIGS. 8a to 8c. The computer device may comprise a desktop computer, a laptop computer, a tablet computer, a smartphone, and combinations thereof. A power source, for example one or more batteries, may be provided in the nosepiece 54, on the PCB, or remotely via a power cable.

The system 50 may further comprise a liner 58 adjustably attachable to one or both of the nosepiece 54 and the eyeglasses 52 between the LEDs 56 and the user's nose. One or both of the nosepiece 54 and the liner 58 may be consumable or disposable after use, while the eyeglasses 52 may be reusable. One or both of the nosepiece 54 and the liner 58 may be deformable to adjustably conform to the user's nose. A plurality of different adjustable nosepieces 34 and/or liners 58 having different shapes and lengths may be provided to accommodate different nose shapes and sizes. One or both of the nosepiece 54 and the liner 58 may be wholly or partially preformed to adjustably conform to the user's nose. One or both of the nosepiece 54 and the liner 58 may comprise a flexible material supported by a deformable frame 60, 62 respectively. The flexible material may, for example, comprise a flexible plastics or rubber material, and the deformable frame 60, 62 may, for example, comprise a deformable metal material. The liner 58 is transmissive to light, for example by comprising a transparent or translucent material, and/or cut-outs in the material. The deformable frame 60, 62 may be positioned outside of the treatment zone, and/or may comprise cut-outs to enable light transmission through the frame. One or both of the nosepiece 54 and the liner 58 may be adjustably attachable to the eyeglasses 52 or one another by releasable fasteners, for example, magnetic fasteners, studs, press-fit fasteners, etc.

One or both of the nosepiece 54 and the liner 58 may have an inverted T-shape, and may comprise a stem extending vertically downwards from the forehead over a tip of the user's nose, and a pair of wings extending horizontally from a lower end of the stem over a pair of nostrils of the user's nose. In other embodiments, the liner 58 may have the inverted T-shape and the nosepiece 54 may have a triangular curved shape. The eyeglasses 52 may have one or more adjustable attachment features, for example slots, guide ridges, holes, posts or projections, for adjustably attaching one or both of the nosepiece 54 and the liner 58 to the eyeglasses 52.

Embodiments of the present invention provide a phototherapy system and related method of treatment that are useful for treating cosmetic and functional nasal disorders.

For the purpose of this specification, the word "comprising" means "including but not limited to," and the word "comprises" has a corresponding meaning.

The above embodiments have been described by way of example only and modifications are possible within the scope of the claims that follow.

The invention claimed is:
1. A system, comprising:
a support adapted to be worn on a head and support a light source to administer an effective amount of light to a nose of the head sufficient to treat a nasal disorder; and
an adjustable nosepiece adapted to support the light source, wherein the adjustable nosepiece has an inverted T-shape and comprises a stem adapted to extend vertically downwards from the forehead over a tip of the nose, and a pair of wings extending horizontally from a lower end of the stem and adapted to extend over a pair of nostrils of the nose.

2. The system of claim 1, wherein the support is further adapted to adjustably or conformably support the light source in contacting or non-contacting relationship with one or more internal nasal surfaces, external nasal surfaces, or combinations thereof.

3. The system of claim 1, wherein the support comprises a feature selected from a headband, a headset, a hat, an eyeglass frame, a goggle frame, a face mask, or combinations thereof.

4. The system of claim 3, wherein the support further comprises one or more eye shields.

5. The system of claim 1, wherein the light source comprises one or more light emitting diodes (LEDs), laser diodes, or combinations thereof.

6. The system of claim 5, wherein the light source comprises multiple LEDs that are collectively or individually controllable.

7. The system of claim 1, wherein the light has a wavelength between 300 nm and 1000 nm.

8. The system of claim 7, wherein the wavelength is between 600 nm and 860 nm.

9. The system of claim 8, wherein the light has peak intensity at a wavelength around 635 nm.

10. The system of claim 1, wherein the nasal disorder comprises a cosmetic or functional nasal disorder selected from nasal deformity, nasal mass, nasal lipoma, nasal swelling, nasal inflammation, nasal obstruction, nasal congestion, nasal trauma, nasal pain, and combinations thereof.

11. The system of claim 1, further comprising a controller adapted to control the light source.

12. The system of claim 11, wherein the controller is adapted to control one or more parameters of the light source selected from wavelength (nm), light output frequency (continuous versus pulsed), power output (mW), power density (W/cm$^2$), energy density (J/cm$^2$), treatment time, total energy delivered (J), and combinations thereof.

13. The system of claim 11, further comprising a user interface connected to the controller.

14. The system of claim 11, wherein the controller comprises a remote Bluetooth controller to wirelessly control the LEDs.

15. A method of treating a nasal disorder comprising administering light to treat a nasal disorder of a user using the system of claim 1.

16. A system, comprising:

a headband to fit around a forehead of a head;

an adjustable nosepiece extending downwardly from the headband to support LEDs closely adjacent a nose of the head, wherein the adjustable nosepiece has an inverted T-shape and comprises a stem adapted to extend vertically downwards from the forehead over a tip of the nose, and a pair of wings extending horizontally from a lower end of the stem and adapted to extend over a pair of nostrils of the nose.

17. The system of claim 16, wherein the adjustable nosepiece is removably connectable to the headband.

18. A system, comprising:

a headband to fit around a forehead of a head;

an adjustable nosepiece extending downwardly from the headband to support LEDs closely adjacent a nose of the head; and a controller to control the LEDs to administer an effective amount of light to treat a disorder of the nose;

wherein the adjustable nosepiece has an inverted T-shape and comprises a stem adapted to extend vertically downwards from the forehead over a tip of the nose, and a pair of wings extending horizontally from a lower end of the stem and adapted to extend over a pair of nostrils of the nose.

19. The system of claim 18, wherein the stem is adapted to be vertically adjustable over the tip of the nose, and the pair of wings are adapted to be horizontally adjustable over the pair of nostrils.

20. The system of claim 18, wherein the adjustable nosepiece is removably connectable to the headband.

21. The system of claim 18, wherein the controller comprises a remote Bluetooth controller to wirelessly control the LEDs.

* * * * *